(12) United States Patent
Jako

(10) Patent No.: US 6,346,106 B1
(45) Date of Patent: Feb. 12, 2002

(54) INSTRUMENT AND METHOD EMPLOYING SNARE ELECTRODE WINDABLE ABOUT ROTATABLE SPOOL FOR MINIMALLY INVASIVE ELECTROSURGICAL RESECTION

(76) Inventor: Geza J Jako, 169 E. Emerson St., Melrose, MA (US) 02176

( * ) Notice: Subject to any disclaimer, the term of this patent is extended or adjusted under 35 U.S.C. 154(b) by 0 days.

(21) Appl. No.: 09/379,084

(22) Filed: Aug. 23, 1999

(51) Int. Cl.[7] ............................................. A61B 18/18
(52) U.S. Cl. .......................................................... 606/47
(58) Field of Search ............................... 606/41, 45–49

(56) References Cited

U.S. PATENT DOCUMENTS

| | | | | |
|---|---|---|---|---|
| 4,294,254 A | * | 10/1981 | Chamness ..................... | 606/47 |
| 5,501,654 A | * | 3/1996 | Failla et al. ................. | 600/204 |
| 5,836,947 A | * | 11/1998 | Fleischman et al. .......... | 606/47 |
| 6,050,995 A | * | 4/2000 | Durgin ......................... | 606/47 |
| 6,235,026 B1 | * | 5/2001 | Smith ........................... | 606/46 |

* cited by examiner

*Primary Examiner*—Michael Peffley

(57) ABSTRACT

A surgical instrument includes a body, a snare electrode, a spool and an electrical connector. A distal part of the body includes a passageway extending axially therethrough. The snare electrode is adapted to telescope in the passageway. The distal part of the body has an outward surface electrically insulated from the snare electrode. A second portion of the snare electrode is extendable from a second port of the passageway for forming a loop sized to be placed over tissue (e.g., portion(s) of the uterus and/or kidney(s), spleen, pancreas, gallbladder, remnant from the liver, and/or vascular aneurysm) to be removed from a patient. The spool is rotatably supported in a proximal part of the body. A first portion of the snare electrode is windable about the spool. A rotation of the spool in a winding direction causes retraction of the first portion of the snare electrode from a first port of the passageway, thereby closing the loop to engage the tissue. The electrical connector is for allowing the snare electrode to be coupled to an electrical source. An electrical current is passed from the electrical source to the loop to cauterize the tissue.

43 Claims, 6 Drawing Sheets

INSTRUMENT AND METHOD EMPLOYING SNARE ELECTRODE WINDABLE ABOUT ROTATABLE SPOOL FOR MINIMALLY INVASIVE ELECTROSURGICAL RESECTION

TECHNICAL FIELD

This invention relates, generally, to surgical instrumentation and, more particularly, to a surgical instrument for electrosurgical resection.

BACKGROUND OF THE INVENTION

The medical field has developed various ways of removing tissue from patients. During surgery, medical practitioners may employ an instrument called a "snare', in order to remove growths such as polyps. A snare may include a handle and a wire loop. Generally, the wire loop may be controlled by a mechanism in the handle for removal of a growth.

Some surgical instruments utilize electricity. One known surgical snare for removing a polyp includes a proximal finger grip assembly. In particular, a finger grip is slidably mounted for movement between a proximal thumb grip and a spacer block, which is located at the proximal end of a distal, nonconductive, stem assembly. Namely, the stem assembly has a first tube engaged proximally by the spacer block and connected distally to a second tube. Further, the second tube forms a sheath for a lead and loop assembly. The lead can be a wire cable removably connected proximally to a clamping knob of the finger grip assembly, which includes an insulated electrical connector for conducting cutting and coagulation current to the lead and loop assembly in order to remove a polyp over which the loop has been placed. Such a design is disclosed in U.S. Pat. No. 3,828,790 to Curtiss et al. (entitled "Surgical Snare," issued Aug. 13, 1974, and assigned to American Cystoscope Makers, Inc.).

One known monopolar electrosurgical instrument for removal of a pedunculated polyp has a proximal handle member and a distal flexible tube. The flexible tube has an outside diameter sufficiently small to fit through the working lumen of an endoscope-type device. A metallic ring-type surface electrode is mounted near the distal end of the flexible tube. The ring-type electrode is coupled to a first electrical cord which the surgeon can couple to an electrosurgical generator in order to perform coagulation. Furthermore, the surgeon can decouple the first electrical cord from the electrosurgical generator, and instead couple thereto a second electrical cord that is coupled to a pull-wire mounted in a bore formed in the handle member. The pull-wire extends distally through the lumen of the flexible tube and is attached to a loop of bare, electrically conductive wire. Hence, by coupling the second electrical cord to the electrosurgical generator, the surgeon can perform cutting of a pedunculated polyp surrounded by the wire loop. Such a design is disclosed in U.S. Pat. No. 5,158,561 to Rydell et al. (entitled "Monopolar Polypectomy Snare With Coagulation Electrode," issued Oct. 27, 1992, and assigned to Everest Medical Corporation).

A need exists for increasing the precision and effectiveness of cauterization and coagulation using surgical snares. A further need exists for decreasing invasiveness and increasing safety in performing hysterectomies (of which over six hundred thousand are performed in the United States each year), laparoscopic surgeries, and resections of the kidney, spleen, and pancreas. Moreover, it is often desirable to remove a relatively large tumor, for instance, on the uterus (e.g., myofibroma or leiomyoma).

SUMMARY OF THE INVENTION

Pursuant to the present invention, the shortcomings of the prior art are overcome and additional advantages provided through the provision of surgical instrumentation that includes an electrosurgical instrument.

In one aspect of the invention, a surgical instrument includes a body, a snare electrode, a spool and an electrical connector. The body has proximal and distal parts. The distal part of the body includes a passageway extending axially therethrough. The passageway has first and second ports. The snare electrode is adapted to telescope in the passageway. The distal part of the body has an outward surface electrically insulated from the snare electrode. The snare electrode includes first and second portions. The second portion of the snare electrode is extendable from the second port of the passageway for forming a loop sized to be placed over tissue to be removed from a patient. The spool is rotatably supported in the proximal part of the body. The first portion of the snare electrode is windable about the spool. A rotation of the spool in a winding direction causes retraction of the first portion of the snare electrode from the first port of the passageway, thereby closing the loop to engage the tissue. The electrical connector is for allowing the snare electrode to be coupled to an electrical source. An electrical current is passed from the electrical source to the loop to cut and cauterize the tissue.

In another aspect of the invention, an outward surface of the proximal part of the body can be electrically insulated from the snare electrode and/or adapted for handling. A driver can be adapted for engagement with the spool. The driver can motivate rotation of the spool.

The driver can allow user switching among operating modes. The operating modes can include first and/or second selections. The first selection can allow winding of a section of the snare electrode about the spool for closing the loop to engage the tissue. The second selection can allow unwinding of a section of the snare electrode from the spool for placing the loop over the tissue and/or relocating the loop.

The proximal part of the body can include and/or be removably engaged with the driver. The driver can be adapted to be coupled with a power source. The power source can include an electrical source, a battery, and/or physical input. The driver can include a electromechanical driver and/or a manual winding mechanism. The manual winding mechanism can comprise the proximal part of the body.

A casing for the driver can include an outward surface electrically insulated from the snare electrode and/or a handle. The spool can include a socket and/or a slot for receiving a shaft of the driver.

The proximal and/or distal parts of the body can include an autoclavable portion. The proximal and/or distal parts of the body can include a disposable portion. The snare electrode can include solid wire, braided wire, and/or fine line cutting wire. The electrical source can allow a selection of at least one electrical frequency for a cauterization of the tissue and/or a coagulation of blood vessels of the patient.

A companion electrode can be selectively coupled to companion the electrical source and to the patient. The electrode can be removably attachable to a shield and/or a cap. A portion of the spool can be slidably engaged with and/or frictionally engaged with a sidewall of the proximal part of the body. The distal part of the body can include a tube, the tube can form the passageway, and the distal part of the body can be formed with non conductive material. The tube can include an opening for accessing, adjusting, and/or severing the snare electrode. It may include another opening for aspiration of smoke. In yet another aspect of the present invention, a surgical instrument includes a body, a snare electrode, a spool and an electrical connector. The body has proximal and distal parts. The distal part of the body has first and second ports. The snare electrode is adapted to telescope in the passageway. The distal part of the body has an outward surface electrically insulated from the snare electrode. The snare electrode includes first and second portions. The cond portion of the snare electrode is extendable from the second port of the passageway for forming a loop sized to be placed over a resection portion of a uterus.

The resection portion of the uterus is to be removed from a patient. The spool is rotatably supported in the proximal part of the body. The first portion of the snare electrode is windable about the spool. A includes a passageway extending axially therethrough. The passageway rotation of the spool in a winding direction causes retraction of the first portion of the snare electrode from the first port of the passageway., thereby closing the loop to engage the resection portion of the uterus. The electrical connector is for allowing the snare electrode to be coupled to an electrical source. An electrical current is passed from the electrical source to the loop to cauterize the resection portion of the uterus.

The invention further contemplates a method for effecting electrosurgical resection. A snare electrode having first and second portions is selected. A body having proximal and distal parts is selected. The distal part of the body includes a passageway extending axially therethrough. The passageway has first and second ports. The snare electrode is telescoped in the passageway, and the second portion of the snare electrode is extended from the second port of the passageway in order to form a loop, where the first portion of the snare electrode is wound about a spool rotatably supported in the proximal part of the body. The loop is sized for placement around a resection portion of an organ. The resection portion of the organ is to be removed from a patient. The spool is rotated in a winding direction to retract the first portion of the snare electrode away from the first port of the passageway, to close the loop and engage the resection portion of the organ. An electrical current is passed from an electrical source to the loop to cautery cut the resection portion of the organ.

In a further aspect of the invention, the rotating of the spool and/or the passing of the electrical current can serve to coagulate blood vessels of the patient. The rotating of the spool can allow user switching among operating modes. The operating modes can include first and/or second selections. The first selection can allow winding of a section of the snare electrode about the spool for closing the loop to engage the organ. The second selection can allow unwinding of a section of the snare electrode from the spool for placing the loop around the organ and/or relocating the loop. The organ can comprise a uterus, gallbladder, liver and/or blood vessel growth or tonsil.

The present invention can be used in standard and minimally invasive surgery. For example, a trocar used in laparocospic surgery or first and second blades of a surgical retractor can be inserted through a small incision into the patient. The first and second blades can be spread to form an operating window at the incision. The spreading of the first and second blades can allow the distal part of the body to be exposed in the operating window.

Thus, the present invention advantageously provides for electrosurgical resection of tissues including large organs such as the uterus with minimal invasiveness, enhanced precision, increased safety and decreased bleeding.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention will be readily understood from the following detailed description of preferred embodiments taken in conjunction with the accompanying drawings in which:

BEST MODE FOR CARRYING OUT THE INVENTION

In accordance with the principles of the present invention, surgical instrumentation is provided in which a snare electrode having an electrical current there through is mechanically retracted by winding about a spool, to perform electrosurgical resection.

Figure 1:
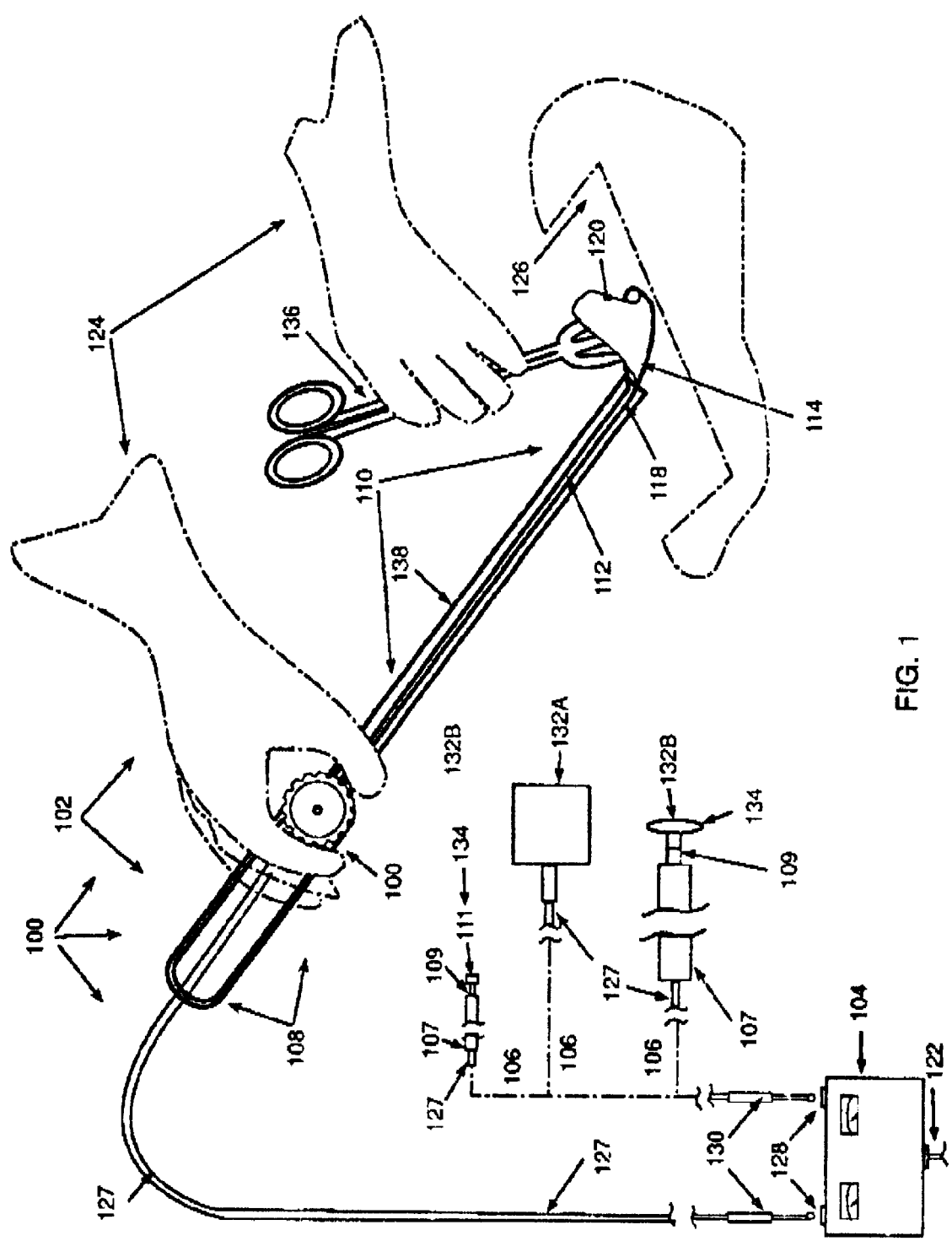
FIG. 1 is a side representation of a use of surgical instrumentation of the present invention.

An example of surgical instrumentation incorporating and using the novel features of the present invention is depicted in FIG. 1 and described in detail herein.

In this exemplary embodiment, surgical instrumentation 100 includes surgical instrument 102, console 104, companion electrode 106 and electrical source 122. The surgical instrument includes proximal part 108, distal part 110, conductive snare electrode 114 and spool 160.

Figure 2:
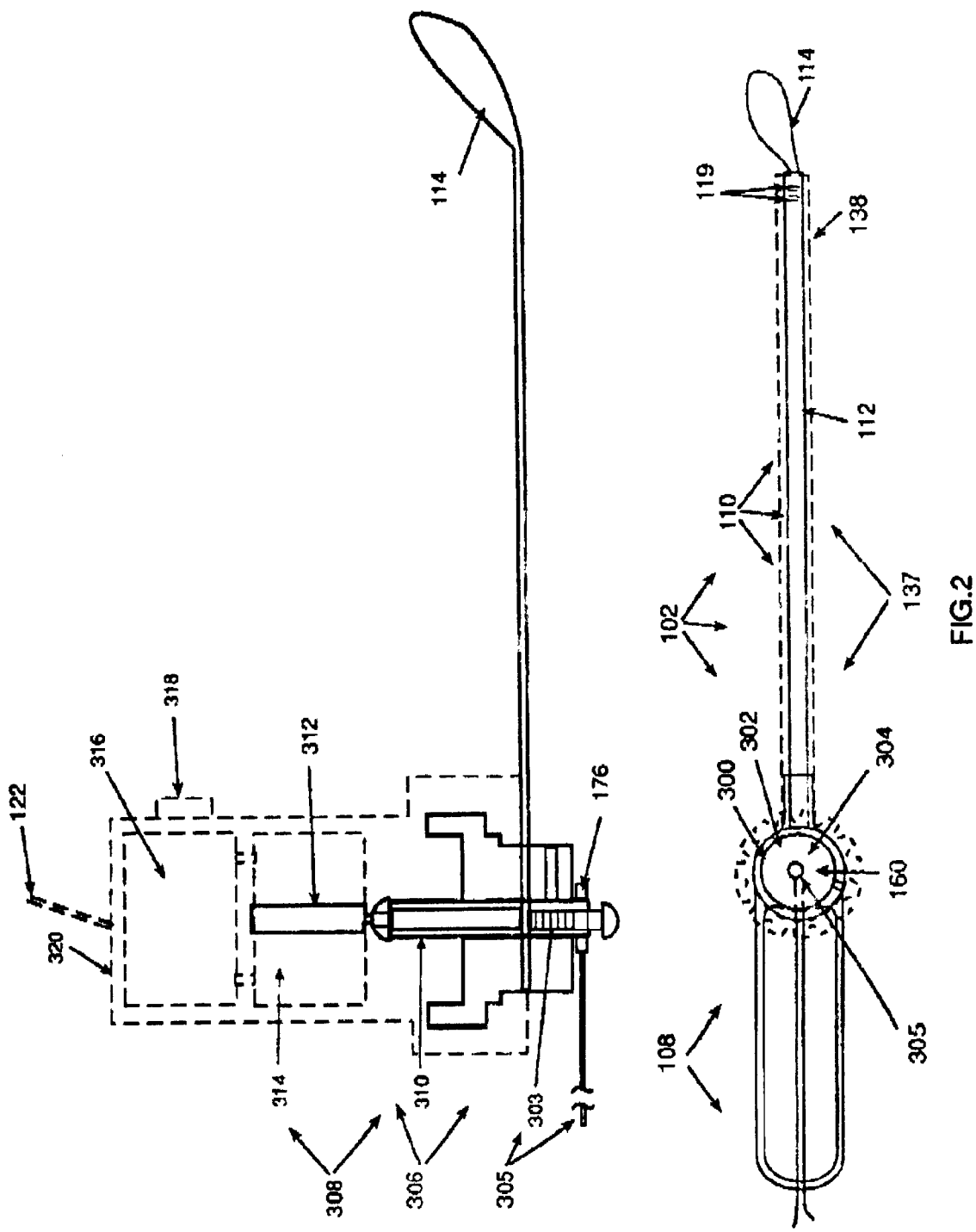
FIG. 2 is a cutaway, elevation, side view, to be partly in section, of one embodiment of an electrosurgical instrument of the surgical instrumentation of FIG. 1, illustrating a snare electrode thereof in a protracted position.

Referring to FIG. 2, snare electrode 114 can be telescoped in passageway 112 of distal part 110, with slots 119. In particular, user (e.g., one or more medical practitioners) 124 (FIG. 1) can extend the snare electrode through the passageway to form a loop. Further, the user can size the loop for placement around targeted tissue 120. As described herein, electrical current may be passed through the loop to cut tissue(s), cauterize wound(s), and/or coagulate blood vessel(s).

Figure 3:
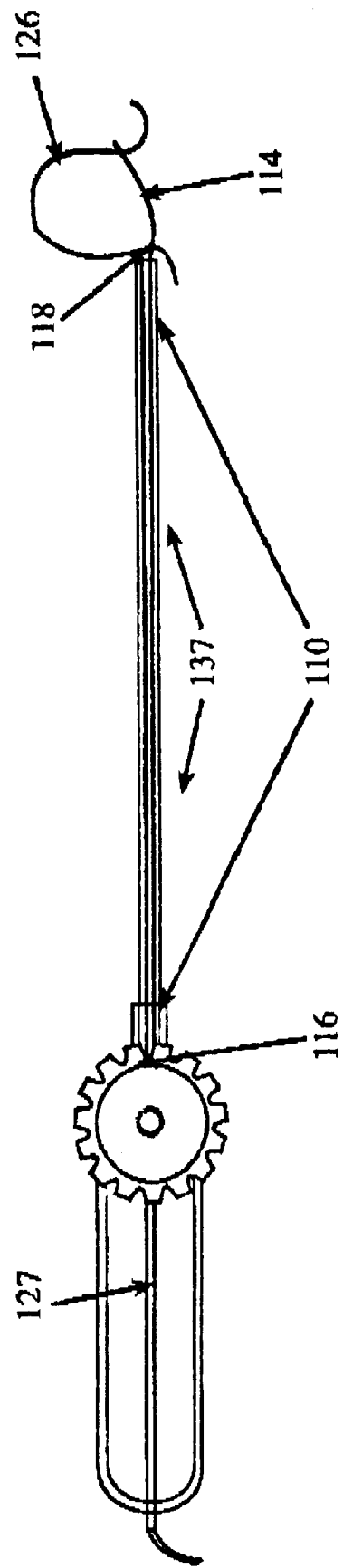
FIG. 3 is a cutaway, elevation, side view, of the electrosurgical instrument of FIG. 2, illustrating the snare electrode in a retracted position.

Referring to FIGS. 2–3, spool 160 may be rotatably disposed in support 300. For example, the support may include housing 302 with chamber 304 which receives the spool. The spool may have (e.g., frictional) relationship(s) with sidewall(s) of the chamber serving to provide selective positioning of the spool and snare electrode 114. For instance, a support interface between flange(s) 305 of the spool and the chamber may hold the spool, and thus the snare electrode, in position until movement thereof is motivated by driver 308, as described herein.

In one example a (e.g., distal) flange 305 (FIGS. 2–3) of spool 160 is reduced (e.g., cut, beveled, or chamfered) in one region thereof to accommodate installation of snare electrode 114 in instrument 102. Whether before, after, or during threading of a distal end of the snare electrode into passageway 112 of tube 137, a proximal end of the snare electrode is preferably mounted or fixed with a set screw 303 in the spool, such as at the midsection thereof. Furthermore, the distal end of the snare electrode may be threaded or inserted through chamber 304, and into the passageway 112, with the spool still outside housing 302. Now, the reduced region of the flange 305 would allow the spool 160 to be inserted or slid into the chamber 304 of the housing 302, notwithstanding the proximal end of the snare electrode being fixed to the spool 160 and the distal end of the snare electrode being threaded into the passageway 112. In particular, once the spool is inserted into the chamber of the housing, (e.g., a middle portion of) the snare electrode may be moved, jostled, or tensioned so the snare electrode is unencumbered by sidewalls of the housing and free for extension, retraction, and rotation, as described herein. Housing 302 may have a port 310.

Referring to FIGS. 2, 2b, 3, spool 160 may be adapted for engagement with drive interface 306 of driver 308. In one example, the drive interface 306 includes shaft 312, which is received by socket (e.g., hex hole or receptacle slot) 310 in the spool. For instance, the socket may be formed integrally (e.g., injection molded) with the spool, or may comprise an (e.g., metal or hard plastic) insert disposed in the spool, depending on factor(s) such as type'(s) of material (s) employed and/or other design and/or use consideration (s).

Still referring to FIGS. 2, 2b, 3, driver 308 may include coupling mechanism (e.g., transmission, gearbox, and/or motor) 314 connected and/or coupled with shaft 312, power source 316, and one or more switches 318, which may permit selection by the user 124 of exemplary "forward" and/or reverse" direction(s) and/or speed(s).

In one example, referring to FIG. 2, a selection of an exemplary "forward" direction for driver 308 serves to extend snare electrode 114 for placement of the loop at an extremity thereof, around targeted tissue 120. Also, referring to FIG. 3, a selection of an exemplary "reverse" direction for the driver serves to retract the snare electrode to close the loop, when the loop is placed around the targeted tissue for cauterization thereof, as described herein.

Referring again to FIGS. 2–5, casing 320 may serve to house or cover driver 308, as well as to provide a handle for gripping and/or manipulation of instrument by the user 124 (FIG. 1). Power source 316 may include, for instance, one or more rechargeable, recyclable, or disposable batteries. In an alternative embodiment, the power source 316 may comprise and/or be connectable with an external source, such as electrical source 122 depicted in FIG. 1, and/or allow powering by the user(s) 124 as discussed below with reference to FIG. 6.

Figure 5:
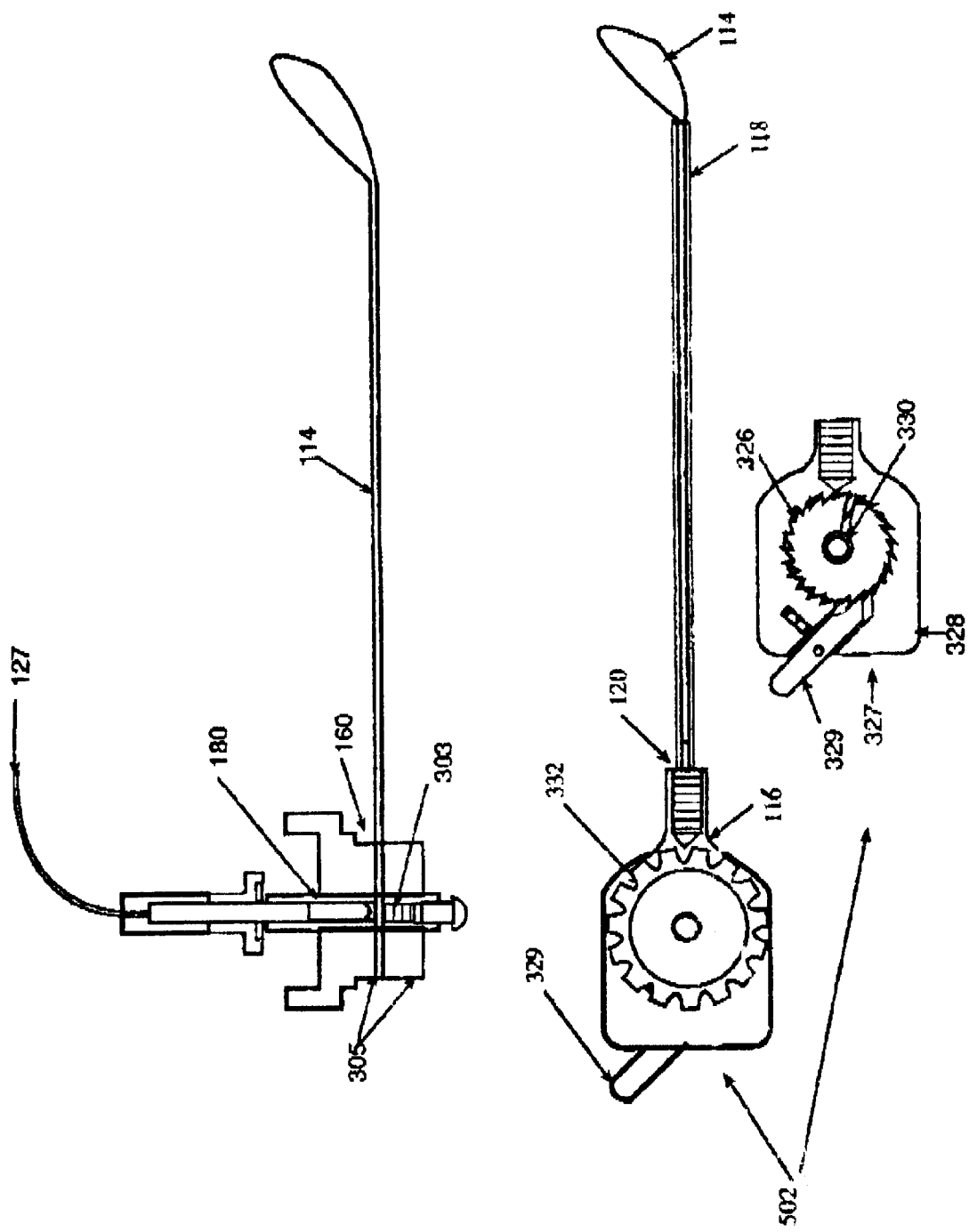
FIG. 5 is a cut away, elevation, partial, side view partly in section of another embodiment of the electrosurgical instrumentation with ratchet and pawl.

Referring to FIG. 5, driver 308 of another exemplary embodiment, namely, surgical instrument 402, may include (e.g., manual) winding mechanism 324. In one example, the winding mechanism includes ratchet wheel 326 mounted on shaft 312, where the ratchet wheel and shaft may be selectively locked against or released for angular rotation, thereby correspondingly setting or relaxing an operative length and/or tightness for snare electrode 114, such as through activation or operation of lock 327. For instance, the lock may comprise pawl 328, which can be meshed with or released from the ratchet wheel by movement of lever 329 or by a (e.g., spring or mass) bias formed in the lock.

Additionally, the shaft may be rotated by turning arm 330 fixed to the shaft, through orbiting thereabout of handle 332 connected with the arm at a position offset radially from the shaft.

As will be appreciated by those skilled in the art, feature (s), component(s), characteristic(s), aspect(s) and/or advantage(s) of instrument 102 and/or instrument 502 described herein in any exemplary embodiment may appropriately be applied and/or extended to any embodiment in accordance with the principles of the present invention. Furthermore, design choice(s) allow numerous variation(s), modification(s), and/or enhancement(s) to exemplary operation(s), use(s), and/or configuration(s) of instrument 102, 502 and/or surgical instrumentation 100 discussed herein.

Again referring to FIGS. 2–5, when the loop is positioned over the targeted tissue 120, the user 124 can operate driver 308 to wind a portion of snare electrode 114 about spool 160, and close the loop to engage the targeted tissue. Furthermore, the user can pass electrical current from an electrical source 122 (FIG. 1) to the loop, for cauterization of the targeted tissue, as described herein.

Figure 4:
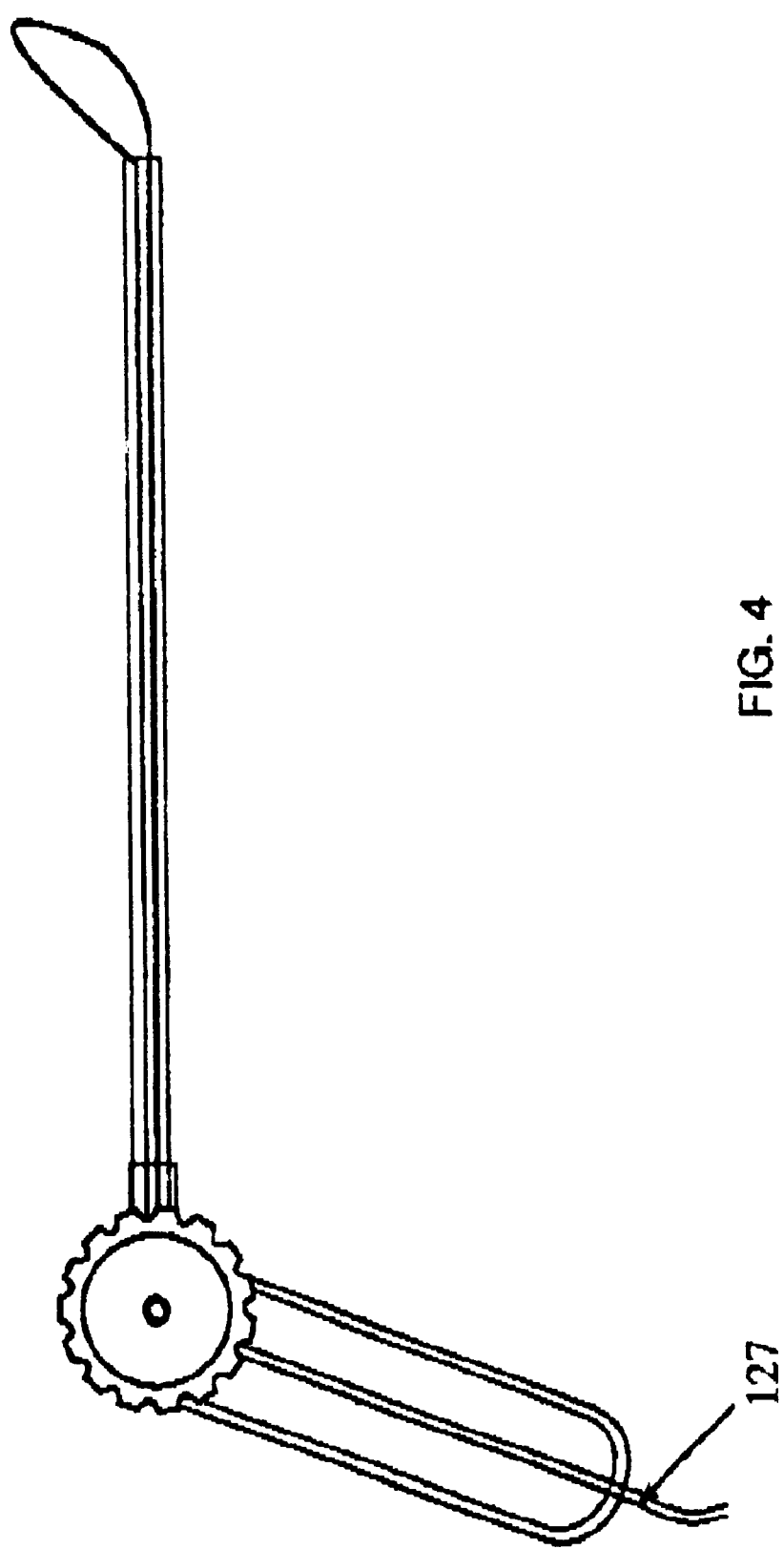
FIG. 4 is a cutaway, elevation, partial, side view, partly in section, of another embodiment of an electrosurgical instrument of the surgical instrumentation of FIG. 1.

As depicted in FIGS. 214 4, distal part 110 of instrument 102 may include tube 137 having passageway 112 extending axially therethrough, tube 137 may include distal slots 119. In one example, the tube 137 might have approximate dimensions such as 20 to 40 cm length, 0.5 to 1 cm width (e.g., diameter), and 0.5 to 2 mm sidewall thickness. However, instrument 102 may be of various sizes depending upon, for example, the type(s) of surgery to be performed. Further, the tube may be suited to selected configuration(s) of snare electrode 114.

As depicted in FIG. 4 tube 137 may originate from proximal part at an angle.

Preferably, insulating material 138 electrically insulates the exterior of distal part 110 and slots 119 from a portion of snare electrode 114 when telescoped in the passageway. Desirably, tube 137 and the insulating material serve to safeguard patient 126 (FIG. 1) from undesired contact with snare electrode 114 which may conduct an electrical current therethrough. Namely, the snare electrode can be telescoped through the passageway of the tube, which can isolate, and whose insulating material can insulate, the snare electrode from unintended contact with the patient. In one example, the tube can be formed from (e.g., integrally with) the insulating material. For instance, the tube might be formed with plastic.

In addition, passageway 112 preferably has first port 116 and second port 118. As depicted in FIG. 2, snare electrode 114 can be extended from the second port for forming a loop sized to be placed over object or targeted tissue 120. For example, the targeted tissue might include a tumor (e.g., myofibroma or leiomyoma)and/or an organ (e.g., the uterus of a female) or any portion of that organ. Further, the snare electrode can be retracted from the first port, as depicted in FIG. 3, and controllably coupled to electrical source 122 for electrosurgical resection of, and/or at, the targeted tissue, as discussed in detail herein.

In one preferred embodiment, various components of instrument 102 are removably attached to allow replacement and/or cleansing thereof between surgical procedures. For example, snare electrode 114 (e.g., inserted in the instrument at a factory), tube 137, housing 302, spool 160, electrical connector 176 and skirt 320 might be assembled as a disposable unit, designed for one-time use. Furthermore, casing 320 might be autoclavable. In another aspect, instrument 502 might be disposable, with exterior portion(s) formed from plastic.

Referring to FIG. 1, snare electrode 114 can be coupled to electrical connector 176 for conducting electrical current thereto. Further, the electrical connector can be coupled to an insulated lead 127, which can be in turn coupled to electrical source 122, so that electrical current conducted by the insulated lead will flow through the snare electrode. In one example, the electrical connector 176 can include a conductive arm mounted in housing 302. The conductive arm extends into the housing 302 to contact the snare electrode.

Referring to FIGS. 2–4, the conductive arm can include female-type connector 180 for mating with a (e.g., banana plug) plate wire connector 181 of the insulated lead. Preferably, insulating material serves to electrically insulate exterior surface(s) of the conductive arm between the housing 302 and the insulated lead 127. In addition, a removable, insulated cap (not shown) might be used for covering any otherwise exposed portion (e.g., the female-type connector) of the conductive arm.

For purposes of illustration, FIG. 1 depicts electrical connector 176 mounted at and/or extending from a "right-hand" side, relative to user 124, of instrument 102. Also, for explanatory purposes, FIGS. 2–4 illustrate the electrical connector 176 mounted at and/or extending from a "left-hand" side, relative to the user, of the instrument 102, 502.

Referring again to FIG. 1, further exemplary description of how snare electrode 114 is electrically activated follows. An electrical current supply console 104 is connected to surgical instrument 102 and companion electrode 106. The companion electrode may serve as a companion-return electrode, as discussed herein. The console 104 provides an electrical current to the instrument 102 and is connected to a typical hospital power supply outlet via lead 127. Console 104 provides a selection and/or range of electrical currents and/or frequencies, or modes of operation. Furthermore, the console 104 might include a number of display(s) and/or signal(s) for measuring and/or monitoring current(s) supplied to the instrument 102. The console might also provide analog and/or digital setting(s) and/or display(s).

In one example, console 104 might comprise a product available from Erbe U.S.A., Inc. (Marietta, Ga.) and sold under the trade designation ERBOTOM ICC 350. This type of console provides modes for cutting, coagulation, and blended mixing of cutting and coagulation.

Instrument 102 and/or companion electrode(s) 106 may be connected to console 104 through, for example, insulated cables or leads 127 and plugs or prongs 130 thereon which plug into sockets 128 of the console.

Referring to FIG. 1, in one aspect, medical practitioner(s) 124 may operate instrument 102 in a monopolar" mode where companion electrode 106 acts as a "ground" or "returning" electrode, and may be contacted on the skin of patient 126 in a monopolar" configuration using exterior plate 132A. For instance, in the monopolar" mode, the "ground" or "returning" electrode may have a large surface area and be taped to the buttocks of the patient. Various gels, electrolytes and/or the like, and/or techniques (e.g., abrasion) for improving electrical conductivity, might be employed at a selected site of the patient, as will be appreciated by those skilled in the art.

Alternatively, still referring to FIG. 1, the instrument 102 may be used in a "bipolar" mode where the companion electrode 106 may have a head 132B which is placed within patient 126 during surgery. The "bipolar" head 132B might be attachable to attachment 134 having variable type, size, and/or shape. The companion electrode can include, for example, an insulated handle 107 or the like for facilitating and safeguarding manipulation of a particular head 132B.

For instance, the attachment 134 might include a spreader or shield 134 which may be used during the surgery to move tissue surrounding the targeted tissue 120 to be resected, and to create more room to operate. Further, a receptacle slot of the "bipolar" head 132B and a stem of the attachment 134 might have mating screwthreads. For example, the shield 134 might safeguard patient 126 while companion electrode 106 is passed (e.g., in the cervical canal of a female for surgery to resect a uterus) to a desired interior location of the patient, to complete the electrical circuit. The shield 134 might have any desired dimension(s). An exemplary shield 134 might be disk-shaped with a transverse dimension (e.g., a diameter) which is sufficient to allow the shield 134 to separate or move tissue(s) away from an organ to be resected. For example, in the case of resection of the uterus, the shield 134 may separate surrounding tissues from the uterus so that the instrument 102 and/or the companion electrode 106 may be maneuvered into the proper position. The attachment 134 may comprise a cap 111.

As will be appreciated by those skilled in the art, given companion electrode 106 might perform ablation and/or coagulation. For instance, ablation might be accomplished using electrode(s) 106, console 104, instrument 102, and/or attachment(s) 134.

Figure 6:
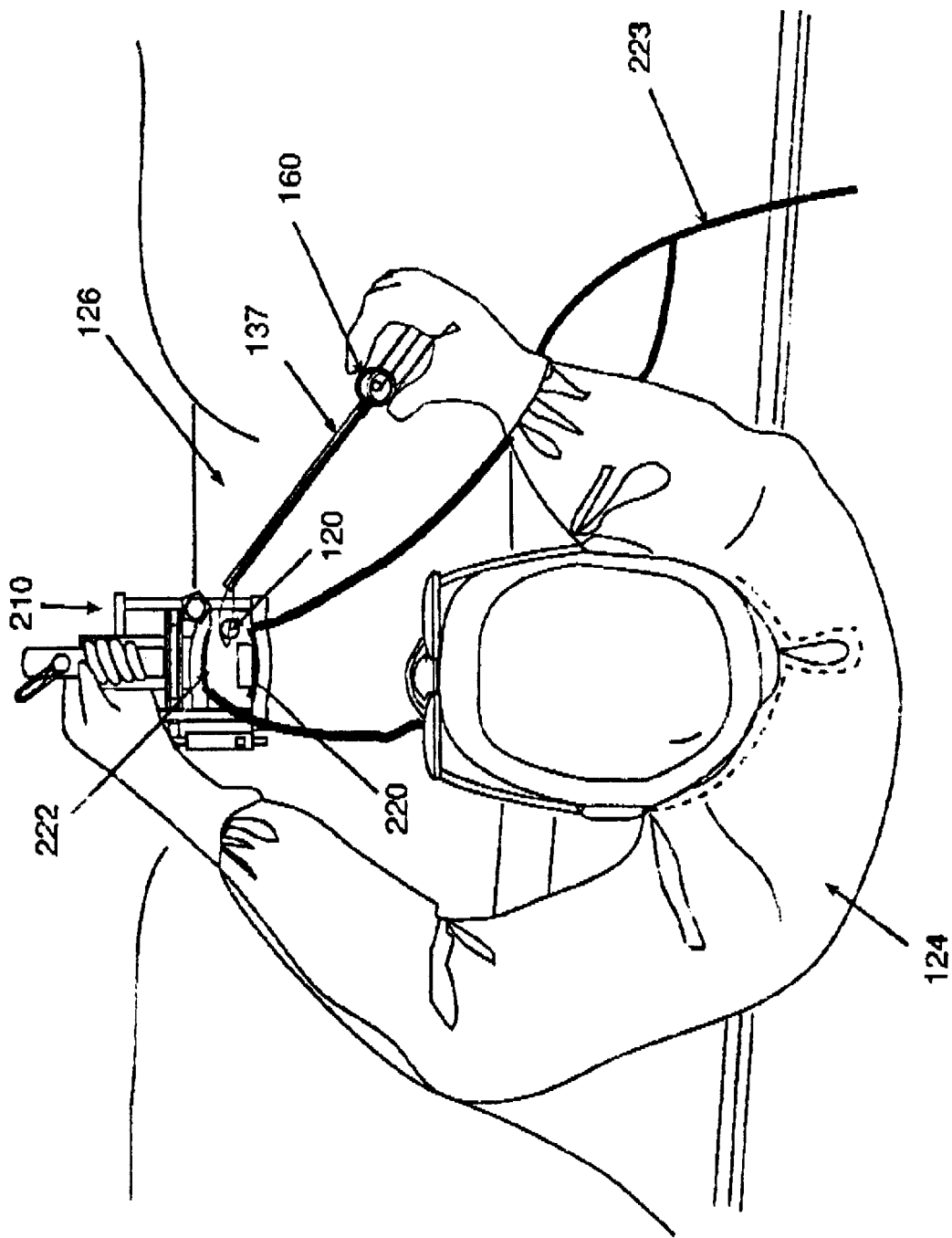
FIG. 6 is a top representation of a use of a retractor endoscope.

Referring to FIGS. 1 and 6, surgical instrumentation 100 might be used with a number of cooperating tools or devices 136. Exemplary cooperating devices include forceps, retractors, "scopes" and the like. In one embodiment, medical practitioners 124 use the surgical instrumentation 100 in conjunction with a device of the type disclosed in U.S. Pat. Nos. 5,503,617 and 5,813,978 to Jako (entitled "Retractor and Method for Direct Access Endoscopic Surgery," issued Apr. 2, 1996 and Sep. 29, 1998), which is hereby incorporated herein by reference in its entirety. Such a device may be referred to as the "JAKOSCOPE"®, or retractor endoscope 210 (FIG. 6). An exemplary use of the retractor endoscope 210 with the surgical instrumentation 100 is discussed below.

As will be appreciated by those skilled in the art, surgical instrumentation 100 enables advantageously improved surgical performance with desirably minimized invasiveness to patient 126. An exemplary use of the surgical instrumentation is now described.

Medical practitioner(s) 124 first identify targeted tissue 120, for example, the uterus to be removed from a location within patient 126 by a surgical procedure which employs surgical instrumentation 100. The surgery might be performed using a laparoscope or by using certain minimally invasive direct access surgical techniques. In particular, the surgery might employ a retractor endoscope 210 such as the JAKOSCOPE®. The patient might receive general and/or local anesthesia. The medical practitioners, in a minimally invasive surgical technique or laparoscopic surgery, typically use a scalpel or trocar to make an incision into the patient at a suitable location. As represented in FIG. 6, retractor endoscope 210 widens the opening at the incision, for example, without significantly augmenting the incision. First and second blades 220 and 222 of the retractor endoscope might be inserted into and through the incision. Next the blades 220 and 222 are spread or spaced apart and articulated or rotated to create an operating window and workspace illuminated by double fiber optic cables in the patient.

The instrument 102 and/or companion electrode 106, if operated in a "bipolar" mode, might be passed through the incision. Such a technique may be used in the abdomen to remove a relatively large tumor (e.g., myofibroma or leiomyoma) 120, or within the uterus of a female. For example, the companion electrode might be passed in the cervical canal of the female. In particular, head 132B and insulated handle 107 may be inserted into and partially through the vagina.

The distal part 110 of instrument 102 may be placed into and through the incision (preferably widened into an operating window created by retractor endoscope 210). For instance, snare electrode 114 may be formed with a (e.g., solid or braided) conductive wire, which can extend through passageway 112 and form a loop. In one example, the conductive wire may be configured to assist in formation of the loop, such as through (e.g., conductive) connection, attachment, or fastening of an end of the wire with another part (e.g., at a selected location, the midpoint, or the opposite end) of the wire. Then, the operative loop might be upwardly limited at a preselected maximal size, as determined by the point of attachment of the wire to itself. Further, such an operative loop may be constricted or closed through retraction (e.g., over a point of self attachment) of the distal end of the snare electrode into the second port 118 of the passageway. The snare electrode can be formed as desired and/or appropriate for selected use(s) and/or application(s).

As represented in FIG. 2, a first portion of snare electrode 114 might be advanced on or unwound from spool 160 through rotation of the spool as motivated by driver 308 operated by user 124, to feed the first portion of the snare electrode distally into first port 116 so a second portion of the snare electrode might be positioned at, or extended or protracted distally from, second port 118. That is, the second portion of the snare electrode might be fed into the first port 116 and through the passageway 112 up to, and as desired, through, the second port 118, leaving the first portion remaining within or outside the passageway 112, such as extending proximally from the first port 116 and/or wound upon the spool.

Referring to FIGS. 2–4, in order to position snare electrode 114 over and around targeted tissue 120, the snare electrode 114, possibly with the assistance of other tools, is manipulated around the tissue to be removed. The snare electrode is formed into a loop of a size to be placed over the tissue and then tightened by rewinding a portion of the snare electrode onto spool 160.

Referring to FIGS. 2–5, the drive interface 306 between socket 310 and shaft 312, optionally in conjunction with a mechanism such as switch 318 FIGS. 2–5) or lock 327 (FIG. 4), may serve to secure snare electrode 114 at a selected length or location, such as when the loop is lassoed over and/or around targeted tissue 120. Referring to FIG. 1, the electrical circuit may be completed by coupling instrument 102, console 104, electrical source 122, companion-return electrode 106, and patient 126.

The appropriate current and electrical frequencies may be selected on the console 104 and the current activated Furthermore, by appropriately winding or unwinding snare electrode 114 with respect to spool 160, the loop formed by the snare electrode 114 is correspondingly tightened or relaxed. As the snare electrode is wound and tightened around targeted tissue 120, the snare electrode cuts the tissue while the current flowing through the loop cauterizes the tissue and coagulates any blood vessels present as a result of the cutting the generated smoke maybe removed by aspiration through slots 119 and port 310. Instrument 102 provides minimally invasive surgery by enhancing precision and bloodlessness in cutting therewith. Desirably, the medical practitioner might coordinate the constriction of the loop about the targeted tissue and the electrical activation of the snare electrode for progressive performance of cauterization and/or coagulation at the targeted tissue.

In addition, snare electrode 114 may be loosened or relaxed through unwinding of the snare electrode from the spool 160, that is, through rotation of the spool in a direction (e.g., "forward") opposite to that used (e.g., "reverse") to wind the snare electrode onto the spool, to allow for repositioning of (e.g., the loop of) the snare electrode.

Referring to FIGS. 1–5, tube 137 may be formed with opening 340—not illustrated—serving to allow access to snare electrode 114, such as for cutting or severing thereof, for instance, in an emergency situation of entanglement or catching inside patient 126 which might otherwise jeopardize health and/or safety.

Snare electrode 114 provides mechanical as well as electrosurgical advantages, in accordance with the principles of the present invention. For instance, fine line cutting wire can be used for the snare electrode to cut more evenly and bloodlessly than with large scissors. Moreover, the electrosurgical coagulation of the blood vessels along with the more precise cutting provide less trauma to patient 126.

Referring to FIG. 1, in "monopolar" operation electrical current(s) may travel, circulate, and/or pass through electrical source 122, console 104, insulated lead 127, electrical connector 176, snare electrode-114, patient 126 and companion-return electrode 106. Insulating material for one or more of tube 137, the electrical connector 176, spool 160, support 300, the insulated lead 127 and/or the console 104 might advantageously serve to electrically isolate exterior and/or exposed surface(s) of surgical instrumentation 100 from the electrical current(s). Therefore, medical practitioner 124 wearing rubber gloves might safely handle and manipulate component(s) of instrument 102, 104 and/or the instrumentation 100 notwithstanding the electrical current(s) flowing therethrough. Moreover, electrically isolated components of the instrument 102, 104 and/or the instrumentation 100 might often contact and/or be coupled to other item(s) and/or one or more entities without danger of conducting the electrical current(s) thereto. The insulating material(s) generally also prevent stray electrical current(s) from undesirably being conducted through the isolated component(s) and to the snare electrode 114, as will be appreciated by those skilled in the art.

Surgical instrumentation 100 might be utilized, for example, in performance of hysterectomies, laparoscopic surgeries, and/or standard or classical operations. In particular, the surgical instrumentation 100 might serve to resect portions (e.g., some or all) of the uterus and/or kidney(s), spleen, pancreas, gallbladder, remnant from the liver, vascular aneurysm or tonsil. For instance, the surgical instrumentation can advantageously decrease invasiveness of removing a relatively large tumor, including malignant tumors, such as might be present on the uterus. When the surgical instrumentation is used to perform hysterectomies, the upper portion of the uterus may be cut to perform a partial resection and/or another cut may be made below the cervix at the cervical fornix for a total resection of the uterus.

In one aspect of the present invention, companion electrode 106 may be operated without attachment 134, and neck 109 (FIG. 1) may be selected to comprise a small conductive (e.g., metal) surface area. The neck may be exposed in order to coagulate certain pathological tissue in the cervical canal, in accordance with the principles of the present invention. Then, the attachment 134 may be connected to the companion electrode 106, such as with mating screw threads, and pressed against the cut cervical surface to provide temporary hemostasis. Preferably, part(s) of the attachment 134 which contact patient 126 are covered or formed with plastic insulator, to avoid potential electric shock. In one example, section(s) of the attachment which do not contact the patient may be formed from metal.

In another aspect, referring to FIG. 1, first companion electrode 106 with attachment 134 can be operated in a "monopolar" mode with a second companion return electrode 106 having exterior head 132A, which may comprise a large adhesive return electrode pad. In particular, the first companion electrode may serve as the active electrode, which may be pressed against the cut stump of the uterine cervix. Furthermore, one may ablate additional tissue, deeper in the cervical canal, by employing the first companion electrode without the attachment connected thereto and with neck 109 exposed, as described above.

Various components of surgical instrumentation are preferably formed from, or have exteriors formed is from, material(s) benign or non-harmful in the surgical environment. For example, heads 132A and 132B, attachment 134, tube 137, socket 310, shaft 312, and/or electrical connector 176 might be formed with a metal such as stainless steel, furthermore, the tube 137, spool 160, support 300, the socket 310, casing 320 and/or various insulator(s) or isolator(s) e.g., for the electrical connector 176) might be formed with plastic, TEFLON®, and/or another (e.g., relatively) non-conductive material(s).

Surgical instrument 100 may have outlet port 306 from chamber 304 through 300 to connect with aspiration tubing for removal of smoke. Tubing 137 may have perforated slots 119 for aspirations of smoke. Such outlet port 306 may be used for insufflation of carbon dioxide or argon gas Moreover, surgical instrumentation 100 might be designed to be partially or totally disposable and/or autoclavable, for enhanced health safety of medical practitioners 124 and patient(s) 126, plus enhanced performance and/or operation of the surgical instrumentation 100. For instance, disposable item(s) might be replaced for each surgical procedure. In one example, distal part 110 of instrument 102 and the second portion of snare electrode 114 might be highly exposed to bodily fluids and/or tissues of the patient 126, so tube 137, support 300, spool 160, electrical connector 176 and snare electrode 114 are preferably designed to be disposable and/or recyclable after processing and/or treatment. Furthermore, remaining component(s) (e.g., casing 320 for driver 308) proximal part 108 of instrument 102, are designed to be autoclavable.

A given part of surgical instrumentation 100 might have any desired characteristics. For instance, a component might be designed to exhibit properties (e.g., hardness, softness, pliability, flexibility, stiffness, rigidity, strength and/or conductivity) suited for an intended and/or expected function and/or purpose.

As will be appreciated by those skilled in the art, electrical source 122 can take any appropriate form. For example, the electrical source 122 might include a power source external to console 104, and/or a number of batteries or sets of batteries, internal and/or external to the console 104. The electrical current(s) and/or one or more frequencies used with the instrument will depend upon the surgery being conducted and the type(s) of tissue(s) being removed. In one example, alternating currents having a minimum frequency of 300 kHz may be employed for electrosurgery.

Numerous alternative embodiments of the present invention exist. Surgical instrumentation 100 might be used in any appropriate procedure(s) and/or on any suitable tissue(s) 120. Also, various components of surgical instrumentation 100 might be formed from any appropriate material(s). Snare electrode 114 and/or head(s) 132A, 132B might have any desired physical properties and/or configuration(s). For example, snare electrode 114 and/or head(s) 132A, 132B might be formed having any desired conductivity and/or constituent material(s). Any portion of surgical instrumentation 100 might be disposable and/or autoclavable. Also, one or more activities of users 124 might optionally be partially or totally accomplished with, or performed through or using, robotics, computerization, embedded systems and/ or automation. Various materials (e.g., which serve as electrical insulators) in surgical instrumentation 100 might serve as chemical and/or electrochemical insulators and/or isolators.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What I claim as my invention is:

1. A surgical instrument, comprising:
    a body having proximal and distal parts, said distal part including a passageway extending axially therethrough, said passageway having first and second ports; with slots;
    a snare electrode adapted to telescope in said passageway, said distal part having an outward surface electrically insulated from said snare electrode; said snare electrode including first and second portions, said second portion being extendable from said second port for forming a loop sized to be placed over tissue to be removed from a patient;
    a spool rotatably supported in said proximal part with port, said first portion of said snare electrode being windable about said spool, wherein a rotation of said spool in a winding direction causes retraction of said first portion of said snare electrode from said first port, thereby closing
    said loop to engage said tissue; and an electrical connector connecting said snare electrode to be coupled to an electrical source, wherein an electrical current is passed from said electrical source to said loop to cauterize said tissue.

2. The instrument of claim 1, wherein an outward surface of said proximal part is at least one of electrically insulated from said snare electrode and adapted for handling.

3. The instrument of claim 1, further comprising a driver adapted for engagement with said spool, wherein said driver can motivate rotation of said spool.

4. The instrument of claim 3, wherein said driver allows user switching among operating modes, wherein said operating modes include at least one of first and second selections, wherein said first selection allows winding of a section of said snare electrode about said spool for closing said loop to engage said tissue, wherein said second selection allows unwinding of a section of said snare electrode from said spool for at least one of placing said loop over said tissue and relocating said loop.

5. The instrument of claim 3, wherein said proximal part at least one of includes and is removably engaged with said driver.

6. The instrument of claim 3, wherein said driver is adapted to be coupled with a power source, and wherein said power source includes at least one of an electrical source, a battery, and physical input.

7. The instrument of claim 3, wherein said driver includes at least one of a electromechanical driver and a manual winding mechanism, wherein said manual winding mechanism comprises said proximal part.

8. The instrument of claim 3, further comprising a casing for said driver, wherein said casing includes at least one of an outward surface electrically insulated from said snare electrode and a handle.

9. The instrument of claim 3, wherein said spool includes at least one of a socket and a slot for receiving a shaft of said driver.

10. The instrument of claim 1, wherein at least one of said proximal and distal parts includes an autoclavable portion.

11. The instrument of claim 1, wherein at least one of said proximal and distal parts includes a disposable portion.

12. The instrument of claim 1, wherein said snare electrode includes at least one of solid wire, braided wire, and fine line cutting wire.

13. The instrument of claim 1 in combination with said electrical source, wherein said electrical source allows a selection of at least one electrical frequency for at least one of a cauterization of said tissue and a coagulation of blood vessels of said patient.

14. An instrument of claim 1 having proximal port for aspiration of smoke or insufflation of gases.

15. The instrument of claim 1 in combination with a companion electrode selectively coupled to said electrical source and adapted to be coupled to said patient.

16. The instrument of claim 15, wherein said companion electrode is removably attachable to at least one of a shield and a cap.

17. The instrument of claim 1, wherein a portion of said spool is at least one of slidably engaged with and frictionally engaged with a sidewall of said proximal part.

18. The instrument of claim 1, wherein said distal part includes a tube, wherein said tube forms said passageway, and wherein said distal part is formed with non-conductive material.

19. The instrument of claim 18, wherein said tube includes an opening for at least one of accessing, adjusting, and severing said snare electrode.

20. The instrument of claim 17, wherein said tube includes slots for aspiration of smoke.

21. A surgical instrument, comprising:
a body having proximal and distal parts, said distal part including a passageway extending axially therethrough, said passageway having first and second ports;
a snare electrode adapted to telescope in said passageway, said distal part having an outward surface electrically insulated from said snare electrode;
said snare electrode including first and second portions, said second portion being extendable from said second port for forming a loop sized to be placed over a resection portion of a uterus, wherein said resection portion is to be is removed from a patient;
a spool rotatably supported in said proximal part, said first portion of said snare electrode being windable about said spool, wherein a rotation of said spool in a winding direction causes retraction of said first portion of said snare electrode from said first port, thereby closing said loop to engage said resection portion of said uterus; and
an electrical connector connecting said snare electrode to be coupled to an electrical source, wherein an electrical current is passed from said electrical source to said loop to cauterize said resection portion of said uterus.

22. The instrument of claim 21, wherein an outward surface of said proximal part is at least one of electrically insulated from said snare electrode and adapted for handling.

23. The instrument of claim 21, further comprising a driver adapted for engagement with said spool, wherein said driver can motivate rotation of said spool.

24. The instrument of claim 23, wherein said driver allows user switching among operating modes, wherein said operating modes include at least one of first and second selections, wherein said first selection allows winding of a section of said snare electrode about said spool for closing said loop to engage said resection portion, wherein said second selection allows unwinding of a section of said snare electrode from said spool for at least one of placing said loop over said resection portion and relocating said loop.

25. The instrument of claim 23, wherein said proximal part at least one of includes and is removably engaged with said driver.

26. The instrument of claim 23, wherein said driver is adapted to be coupled with a power source, and wherein said power source includes at least one of an electrical source, a battery, and physical input.

27. The instrument of claim 23, wherein said driver includes at least one of a electromechanical driver and a manual winding mechanism, wherein said manual winding mechanism comprises said proximal part.

28. The instrument of claim 23, further comprising a casing for said driver, wherein said casing includes at least one of an outward surface electrically insulated from said snare electrode and a handle.

29. The instrument of claim 23, wherein said spool includes at least one of a socket and a slot for receiving a shaft of said driver.

30. The instrument of claim 21, wherein at least one of said proximal and distal parts includes an autoclavable portion.

31. The instrument of claim 21, wherein at least one of said proximal and distal parts includes a disposable portion.

32. The instrument of claim 19, wherein said snare electrode includes at least one of solid wire, braided wire, and fine line cutting wire.

33. The instrument of claim 21 in combination with said electrical source, wherein said electrical source allows a selection of at least one electrical frequency for at least one of a cauterization of said resection portion and a coagulation of blood vessels of said patient.

34. The instrument of claim 21 in combination with a companion electrode selectively coupled to said electrical source and to said patient.

35. The instrument of claim 21, wherein said companion electrode is removably attachable to at least one of a shield and a cap.

36. The instrument of claim 21, wherein a portion of said spool is at least one of slidably engaged with and frictionally engaged with a sidewall of said proximal part.

37. The instrument of claim 21, wherein said distal part includes a tube, wherein said tube forms said passageway, and wherein said distal part is formed with non-conductive material.

38. The instrument of claim 37, wherein said tube includes an opening for at least one of accessing, adjusting, and severing said snare electrode.

39. A method of effecting electrosurgical resection, said method comprising: selecting a snare electrode having first and second portions; selecting a body having proximal and distal parts, said distal part including a passageway extending axially therethrough, said passageway having first and second ports; telescoping said snare electrode in said passageway and extending said second portion of said snare electrode from said second port in order to form a loop, said first portion of said snare electrode being wound about a spool rotatably supported in said proximal part; sizing said loop for placement around a resection portion of an organ, wherein said resection portion is to be removed from a patient; rotating said spool in a winding direction to retract said first portion of said snare electrode away from said first port, to close said loop and engage said resection portion of said organ; and passing an electrical current from an electrical source to said loop to cauterize said resection portion of said organ.

40. The method of claim 39, further comprising:

inserting first and second blades into an incision of said patient; and spreading said first and second blades to form an operating window at said incision, wherein said spreading allows said distal part to be disposed in said operating window.

41. The method of claim 39, wherein at least one of said rotating and said passing serves to coagulate blood vessels of said patient.

42. The method of claim 39, wherein said rotating allows user switching among operating modes, wherein said operating modes include at least one of first and second selections, wherein said first selection allows winding of a section of said snare electrode about said spool for closing said loop to engage said organ, wherein said second selection allows unwinding of a section of said snare electrode from said spool for at least one of placing said loop around said organ and relocating said loop.

43. The method of claim 39, wherein said organ comprises at least one of a uterus, gallbladder, liver and blood vessel growth and tonsil.

* * * * *